United States Patent
Bridges et al.

(10) Patent No.: US 8,563,587 B2
(45) Date of Patent: Oct. 22, 2013

(54) METHODS AND COMPOSITIONS FOR TREATING FISH DISEASES

(75) Inventors: Michael A. Bridges, Seattle, WA (US); Christine M. Palczewski, Seattle, WA (US); James R. Scott, Bellevue, WA (US); Jeremy Suess, Los Angeles, CA (US); Everett J. Nichols, Edmonds, WA (US)

(73) Assignee: HaloSource, Inc., Bothell, WA (US)

( * ) Notice: Subject to any disclaimer, the term of this patent is extended or adjusted under 35 U.S.C. 154(b) by 956 days.

(21) Appl. No.: 12/280,786

(22) PCT Filed: Feb. 28, 2007

(86) PCT No.: PCT/US2007/063000
§ 371 (c)(1),
(2), (4) Date: Feb. 27, 2009

(87) PCT Pub. No.: WO2008/115225
PCT Pub. Date: Sep. 25, 2008

(65) Prior Publication Data
US 2009/0239907 A1    Sep. 24, 2009

Related U.S. Application Data

(60) Provisional application No. 60/777,652, filed on Feb. 28, 2006.

(51) Int. Cl.
*A01N 43/50* (2006.01)
*A61K 31/415* (2006.01)
*C07D 233/00* (2006.01)

(52) U.S. Cl.
USPC .................................. 514/385; 548/316.4

(58) Field of Classification Search
USPC .................................. 514/385; 548/316.4
See application file for complete search history.

(56) References Cited

U.S. PATENT DOCUMENTS

| | | | |
|---|---|---|---|
| 4,927,546 A | 5/1990 | Wiedrich | |
| 5,057,612 A | 10/1991 | Worley | |
| 5,126,057 A * | 6/1992 | Worley et al. | 504/156 |
| 5,490,983 A | 2/1996 | Worley | |
| 5,593,678 A * | 1/1997 | Evans et al. | 424/184.1 |
| 6,852,312 B2 | 2/2005 | Worley | |
| 6,863,830 B1 | 3/2005 | Purdy | |
| 2004/0127667 A1 | 7/2004 | Worley | |

OTHER PUBLICATIONS

Elrod et al. "A facile Synthetic Approach to Imidazolidinone Biocides" Ind. Eng. Chem. Res. 1999, vol. 38, pp. 4144-4149.*
Miller-Chou et al. "A review of polymer dissolution" Prog. Polym. Sci., 2003, vol. 28, pp. 1223-1270.*
International Search Report dated Oct. 1, 2008, issued in corresponding International Application No. PCT/US07/63000, filed Feb. 28, 2007.
Written Opinion of the International Searching Authority dated Oct. 1, 2008, issued in corresponding International Application No. PCT/US07/63000, filed Feb. 28, 2007.

* cited by examiner

*Primary Examiner* — Kendra D Carter
(74) *Attorney, Agent, or Firm* — Christensen O'Connor Johnson Kindness PLLC (57) ABSTRACT

Therapeutic and prophylactic treatments of aquatic species and aquatic diseases through the controlled introduction of a heterocyclic N-halamine into an aquatic habitat.

14 Claims, 3 Drawing Sheets

METHODS AND COMPOSITIONS FOR TREATING FISH DISEASES

CROSS-REFERENCE TO RELATED APPLICATION

This application claims the benefit of U.S. Provisional Application No. 60/777,652, filed Feb. 28, 2006, expressly incorporated herein by reference in its entirety.

FIELD OF INVENTION

The invention is related to the therapeutic and prophylactic treatment of aquatic diseases of all varieties through the controlled introduction of a heterocyclic N-halamine, such as 1-chloro-2,2,5,5-tetramethylimidazolidin-4-one, into an aquatic habitat.

BACKGROUND OF THE INVENTION

Recent years have seen a flourishing of aquaculture (culture of saltwater fish and freshwater fish) with the attendant outbreaks of various fish diseases. Some fish species are very expensive, and the aquarist would suffer financially if the fish were to fall victim to a disease. Currently, the prevention and treatment of fish diseases, such as pseudotuberculosis, frequently employs antibacterial agents, such as ampicillin, oxolinic acid, and the like. However, the widespread usage of these antibacterial/antibiotic/antifungal agents has resulted in bacteria that are resistant to these antibacterial agents.

There exists, therefore, a need for the development of new agents for the prevention and therapy of fish diseases, which are not based on antibiotics or other conventional drugs, and are active against such resistant microorganisms.

U.S. Pat. No. 5,057,612 (Worley et al.), incorporated herein by reference, describes a class of relatively water-insoluble halogenated imidazolidinones. The compound 1-Chloro-2,2,5,5-tetramethylimidazolidin-4-one (MC) is one such halogenated imidazolidinone described by Worley et al. that stably binds chlorine and/or bromine to tetramethylimidazolidin-4-one. MC is from a class of compounds known as heterocyclic N-halamines. Other well known heterocyclic N-halamines include oxazolidinones and piperidines.

Because of the above described problems in the prior art, there is a widely felt need for new products to treat diseases of an aquatic species.

SUMMARY OF THE INVENTION

One embodiment of the invention provides a composition for treating an aquatic habitat. The composition dissolves according to a solubility profile that produces a slow rise of one or more heterocyclic N-halamines to achieve a concentration of not more than about 20 ppm over a time period of about 6 hours in the aquatic habitat to treat a disease of an aquatic species without killing the aquatic species. The composition can be in the form of a solid tablet, pellet or block comprising one or more heterocyclic N-halamines, and optionally, one or more suitable carriers. Alternatively, the one or more heterocyclic N-halamines can be placed within a device having a porous or permeable material that allows a controlled release of the heterocyclic N-halamines to achieve a concentration of not more than about 20 ppm over a time period of about 6 hours. In other embodiments, the solubility profile of the composition or device is designed for achieving a concentration of not more than about 10 ppm over a time period of about 6 hours of the one or more heterocyclic N-halamines. In other embodiments, the solubility profile of the composition or device is designed for achieving a concentration of not more than about 5 ppm over a time period of about 6 hours of the one or more heterocyclic N-halamines. In other embodiments, the solubility profile of the composition or device is designed for achieving a concentration of not more than about 2 ppm over a time period of about 6 hours of the one or more heterocyclic N-halamines. In other embodiments, the solubility profile of the composition or device is designed for achieving a concentration of not more than about 1 ppm over a time period of about 6 hours of the one or more heterocyclic N-halamines. In other embodiments, the solubility profile of the composition or device is designed for achieving a concentration of not more than about 0.5 ppm over a time period of about 6 hours of the one or more heterocyclic N-halamines. Methods that use any one of the compositions having the solubility profiles above are also described.

Another embodiment of the invention provides a method for treating an aquatic habitat to treat an aquatic disease. The method comprises dosing one or more heterocyclic N-halamines into the aquatic habitat to achieve any one of the solubility profiles a concentration of less than about 20 ppm over a time period of about 6 hours. Other embodiments may use any one of the solubility profiles described above.

In another aspect, one embodiment of the invention provides a method for treating an aquatic species suffering from a water-borne disease. The method comprises dosing one or more heterocyclic N-halamines into the aquatic habitat to produce a concentration of less than about 20 ppm of the one or more heterocyclic N-halamines over a time period of about 6 hours. Other embodiments may use any one of the solubility profiles described above.

Another embodiment of the invention provides a method comprising introducing a solid form of one or more heterocyclic N-halamines in an aquatic habitat to produce a gradual rise in the concentration of the one or more heterocyclic N-halamines in the aquatic habitat to acclimate an aquatic species. By the time the concentration of heterocyclic N-halamine rises to a level effective to treat a pathogen, the aquatic species will be acclimated and will survive the dosage of the heterocyclic N-halamine.

The solubility profiles from about 20 ppm to about 0.5 ppm over a time period of about 6 hours are achieved by any one or more heterocyclic N-halamine.

Heterocyclic N-halamines include N-halo imidizolidinones, N-halo oxazolidinones and N-halo piperidines.

N-halo imidizolidinones include N-halo imidizolidin-4-ones and N-halo imidizolidin-2-ones.

N-halo imidizolidin-4-ones have the formula (I):

wherein X and X' are independently selected from the group consisting of hydrogen, chlorine, and bromine, provided that X and X' are not both hydrogen; and $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen; or $R_1$ and $R_2$ and/or $R_3$ and $R_4$ taken together with the carbon atom to which they are attached form a 5- or 6-membered ring.

Representative N-halo imidizolidin-4-ones include, but are not limited to, 1-chloro-2,2,5,5-tetramethyl imidazolidin-4-one (MC), 1-bromo-2,2,5,5-tetramethyl-4-imidazolidinone, 1,3-dichloro-2,2,5,5-tetramethyl imidazolidin-4-one, 1,3-dichloro-2,5-bis(pentamethylene)imidazolidin-4-one, 1,3-dichloro-2-pentamethylene-5,5-dimethylimidazolidin-4-one, 1,3-dichloro-2,2-dimethyl-5-pentamethyleneimidazolidin-4-one, 1,3-dichloro-2,2-dimethyl-5,5-diethylimidazolidin-4-one, 1,3-dichloro-2-pentamethylene-5,5-diethylimidazolidin-4-one, and 1,3-dichloro-2-pentamethylene-5-ethyl-5-methylimidazolidin-4-one.

N-halo imidizolidin-2-ones have the formula (II):

(II)

wherein X and X' are independently selected from the group consisting of hydrogen, chlorine, and bromine, provided that X and X' are not both hydrogen; and $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo imidizolidin-2-ones include, but are note limited to, N,N'-dihaloimidazolidin-2-ones, such as 1,3-dichloro-4,4,5,5-tetramethyl-2-imidazolidinone and 1,3-dibromo-4,4,5,5-tetramethyl-2-imidazolidinone.

N-halo oxazolidinones include N-halo oxazolidin-2-ones having the formula (III):

(III)

wherein X is selected from the group consisting of chlorine and bromine; and

R1, R2, R3, and R4 are independently selected from the group consisting of hydrogen, C1-C4 alkyl, C1-C4 alkoxy, hydroxy, phenyl, and substituted phenyl, provided that not more than one of the substituents R1-R4 is hydrogen, or R1 and R2 and/or R3 and R4 taken together with the carbon atom to which they are attached form a 5- or 6-membered ring.

Representative N-halo oxazolidinones include, but are not limited to, 3-chloro-4,4-dimethyl-2-oxazolidinone and 3-bromo-4,4-dimethyl-2-oxazolidinone.

N-halo piperidines have the formula (IV):

(IV)

wherein X is a halogen selected from the group consisting of chlorine and bromine; and $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo piperidines include, but are not limited to, 1-chloro-2,2,6,6-tetramethylpiperidine and 1-bromo-2,2,6,6-tetramethylpiperidine.

One embodiment of the invention provides solid forms, such as tablets, pellets, and blocks containing one or more of the above-described heterocyclic N-halamines that can be added directly into an aquatic habitat. The solid forms gradually dissolve and slowly raise the concentration of the one or more heterocyclic N-halamines in the aquatic habitat to an effective level to kill a disease of an aquatic species. Advantageously, the slow rise in the concentration of the one or more heterocyclic N-halamines is believed to acclimate the aquatic species to the one or more heterocyclic N-halamines to prevent killing the aquatic species from the dosage of the one or more heterocyclic N-halamines. Alternatively, particulate forms of one or more heterocyclic N-halamines can be placed in a device having a porous or permeable material that separates the one or more heterocyclic N-halamines from the aquatic habitat, but allows the transfer of the one or more heterocyclic N-halamines to the aquatic habitat in a slow-release manner. The device can release one or more heterocyclic N-halamines to achieve a concentration from not more than about 20 ppm to not more than 0.5 ppm over a time period of about 6 hours.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

The present invention provides compositions and methods to treat an aquatic habitat, and for treating aquatic species to rid them of diseases, and for the prevention of water-borne (aquatic) diseases.

One embodiment of the invention is a composition for treating an aquatic habitat. The composition dissolves according to a solubility profile that produces a slow rise in the concentration of one or more heterocyclic N-halamines in the aquatic habitat to achieve a concentration of the one or more heterocyclic N-halamines of not more than about 20 ppm over a time period of about 6 hours in the aquatic habitat. In other embodiments, the solubility profile of the composition is designed for achieving a concentration of not more than about 10 ppm over a time period of about 6 hours of the one or more heterocyclic N-halamines. In other embodiments, the solubility profile of the composition is designed for achieving a concentration of not more than about 5 ppm over a time period of about 6 hours of the one or more heterocyclic N-halamines. In other embodiments, the solubility profile of the composition is designed for achieving a concentration of not more than about 2 ppm over a time period of about 6 hours of the one or more heterocyclic N-halamines. In other embodiments, the solubility profile of the composition is designed for achieving a concentration of not more than about 1 ppm over a time period of about 6 hours of the one or more heterocyclic N-halamines. In other embodiments, the solubility profile of the composition is designed for achieving a concentration of not more than about 0.5 ppm over a time period of about 6 hours of the one or more heterocyclic N-halamines. The slow rise in the concentration is effective to treat a disease without killing any of the aquatic species in the habitat. Various means can be employed to deliver the one or more heterocyclic N-halamines in a slow release manner. For example, the means can include a tablet, pellet, or block comprising one or more heterocyclic N-halamines, and optionally comprising a suitable carrier. Alternatively, the tablet or pellet can include only the one or more heterocyclic N-halamines. When only the one or more heterocyclic N-halamines comprise the entire tablet, pellet, or block, the one or more heterocyclic N-halamines can be compressed at a higher pressure to achieve similar solubility profiles as compared with the pressure when using a binder.

Heterocyclic N-halamines include N-halo imidizolidinones, N-halo oxazolidinones and N-halo piperidines.

N-halo imidazolidinones include N-halo imidazolidin-4-ones and N-halo imidazolidin-2-ones.

N-halo imidazolidin-4-ones have the formula (I):

(I)

wherein X and X' are independently selected from the group consisting of hydrogen, chlorine, and bromine, provided that X and X' are not both hydrogen; and $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo imidazolidin-4-ones include, but are not limited to, 1-chloro-2,2,5,5,-tetramethyl imidazolidin-4-one (MC), 1-bromo-2,2,5,5-tetramethyl-4-imidazolidinone, 1,3-dichloro-2,2,5,5-tetramethyl imidazolidin-4-one, 1,3-dichloro-2,5 bis(pentamethylene)imidazolidin-4-one, 1,3-dichloro-2-pentamethylene-5,5-dimethylimidazolidin-4-one, 1,3-dichloro-2,2-dimethyl-5-pentamethyleneimidazolidin-4-one, 1,3-dichloro-2,2-dimethyl-5,5-diethylimidazolidin-4-one, 1,3-dichloro-2-pentamethylene-5,5-diethylimidazolidin-4-one, 1,3-dichloro-2-pentamethylene-5-ethyl-5-methylimidazolidin-4-one.

N-halo imidazolidin-2-ones have the formula (II):

(II)

wherein X and X' are independently selected from the group consisting of hydrogen, chlorine, and bromine, provided that X and X' are not both hydrogen; and $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo imidazolidin-2-ones include, but are note limited to, N,N'-dihaloimidazolidin-2-ones, such as 1,3-dichloro-4,4,5,5-tetramethyl-2-imidazolidinone and 1,3-dibromo-4,4,5,5-tetramethyl-2-imidazolidinone.

N-halo oxazolidinones include N-halo oxazolidin-2-ones having the formula (III):

(III)

wherein X is selected from the group consisting of chlorine and bromine; $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo oxazolidinones include, but are not limited to, 3-chloro-4,4-dimethyl-2-oxazolidinone and 3-bromo-4,4-dimethyl-2-oxazolidinone.

N-halo piperidines have the formula (IV):

wherein X is a halogen selected from the group consisting of chlorine and bromine; $R_1$, $R_2$, $R_3$, and $R_4$ are independently selected from the group consisting of hydrogen, $C_1$-$C_4$ alkyl, $C_1$-$C_4$ alkoxy, hydroxy, phenyl, and substituted phenyl, provided that not more than one of the substituents $R_1$-$R_4$ is hydrogen, or $R_1$ and $R_2$ and/or $R_3$ and $R_4$ taken together with the carbon atom to which they are attached form a 5- or 6-membered ring.

Representative N-halo piperidines include, but are not limited to, 1-chloro-2,2,6,6-tetramethylpiperidine and 1-bromo-2,2,6,6-tetramethylpiperidine.

The above-described heterocyclic N-halamines are readily available from commercial sources. Accordingly, the methods for their preparation are not described in this application for the sake of brevity.

One or more heterocylic N-halamines are incorporated into a tablet, pellet, or block, optionally with a carrier. The tablet is manufactured to dissolve according to a solubility profile to provide a slow rise in the concentration of the one or more heterocyclic N-halamines to achieve a concentration of not more than about 20 ppm over a time period of about 6 hours in the aquatic habitat in order to treat a disease of an aquatic species. In other embodiments, the solubility profile of the tablet is designed for achieving a concentration of not more than about 10 ppm over a time period of about 6 hours of the one or more heterocyclic N-halamines. In other embodiments, the solubility profile of the tablet is designed for achieving a concentration of not more than about 5 ppm over a time period of about 6 hours of the one or more heterocyclic N-halamines. In other embodiments, the solubility profile of the tablet is designed for achieving a concentration of not more than about 2 ppm over a time period of about 6 hours of the one or more heterocyclic N-halamines. In other embodiments, the solubility profile of the tablet is designed for achieving a concentration of not more than about 1 ppm over a time period of about 6 hours of the one or more heterocyclic N-halamines. In other embodiments, the solubility profile of the tablet is designed for achieving a concentration of not more than about 0.5 ppm over a time period of about 6 hours of the one or more heterocyclic N-halamines. The above-described concentrations of the one or more heterocyclic N-halamines are effective in treating a disease of an aquatic species and without killing the aquatic species. The heterocyclic N-halamines can be introduced into the aquatic habitat in multiple doses to achieve the effective concentration, or on a continual basis.

The heterocyclic N-halamines can be introduced into the aquatic habitat in a variety of forms. The solid forms can be a tablets, pellets, blocks, particulates, or any solid that contains amounts of one or more heterocyclic N-halamines effective to treat a disease by a gradual dissolution process. In one embodiment, a preferred heterocyclic N-halamine is a N-halo imidazolidinone, preferably MC.

The solid forms can include one or more heterocyclic N-halamines compacted together with one or more suitable carriers or binders. A suitable carrier can be any conventional excipient, such as magnesium sulfate, sodium chloride, cellulose, starch and calcium phosphate. Carriers can assist in binding the one or more heterocyclic N-halamines into a shape. Alternatively, the tablet, pellet or block can include only the one or more heterocyclic N-halamines. When only the one or more heterocyclic N-halamines comprise the entire tablet, pellet, or block, the one or more heterocyclic N-halamines can be compressed at a higher pressure to achieve similar solubility profiles as compared with the pressure when using a binder. Embodiments of the compositions can include 10% by weight or less of one or more heterocyclic N-halamines based on the total weight of the composition. In some embodiments of the compositions, the heterocyclic N-halamines are the sole effective agent that treats a disease, wherein the carrier is not effective to treat the disease. However, in other embodiments of the compositions, one or more antibacterial, antibiotic, or antifungal agents can be included with the one or more heterocyclic N-halamines. The carrier is typically 90% by weight or greater based on the total weight of the composition. As illustrative for use in a home aquarium, a representative tablet may weigh between about 1 to about 2 grams, have a diameter of about ½ to ¾ inches, nominally about ⅝ inch, and a thickness ranging from about 0.2 to about 0.3 inches.

The solid forms containing one or more heterocyclic N-halamines can be added directly to the aquatic habitat or placed in a device. Once in the water, the solid forms will gradually dissolve, which exposes more of the heterocyclic N-halamines to the water, resulting in a gradual release of the one or more heterocyclic N-halamines from the solid form into the water over time. Slowly rising concentrations of the one or more heterocyclic N-halamines in the aquatic habitat is believed to condition aquatic species to the toxic effects of the heterocyclic N-halamines. As a result, the concentration of the heterocyclic N-halamines slowly rises to an effective level to treat a disease of an aquatic species, but does not kill the aquatic species.

In one embodiment, one or more heterocyclic N-halamines can be in a particulate, granular loose form, such as a powder. The powder, granular, or other loose forms of heterocyclic N-halamines can be contained within a slow release device. The device may take the form of a receptacle or container having a porous, permeable or semi-permeable membrane or material separating the one or more heterocyclic N-halamines from the aquatic habitat, but still allowing the transfer of the one or more heterocyclic N-halamines to the aquatic habitat when exposed to water. The device holds the one or more heterocyclic N-halamines, and the porous, permeable, or semi-permeable material acts a means to control the release of the one or more heterocyclic N-halamines into the aquatic habitat according to predetermined solubility profile to achieve the desired concentration. In one embodiment, for example, the device can be a section of a "dialysis" tube or other similar material that allows the passage of compounds of a predetermined molecular weight. The membranes are designed to allow the passage of dissolved compounds, but prevent the passage of particulates or nondissolved compounds. As a guide, the membranes or materials that allow the passage of dissolved compounds in the microparticle size range are suitable. The membranes or materials should prevent the passage of particulates in sizes that may be eaten by the fish. As an approximation, when particles are visible to the human eye, the particle may be large enough to be ingested by fish. Accordingly, membranes or materials need to prevent the passage of such large particles. An approximation of the size of compounds that should be allowed passage are those in the microparticle size range (typically defined between 1 to 20 microns) or smaller. Accordingly, in one embodiment, membranes and materials may allow the passage of compounds smaller than 20 microns. Other embodiments may allow the passage of compounds not larger than 10 microns, 5 microns, 2 microns, and 1 micron. The devices control the release of the one or more heterocyclic N-halamines according to a solubility profile that produces a slow rise of one or more heterocyclic N-halamines to achieve a concentration of not more than about 20 ppm over a time period of about 6 hours in the aquatic habitat to treat a disease of an aquatic species without killing the aquatic species. In other embodiments, the device achieves a concentration of not more than about 10 ppm over a time period of about 6 hours of the one or more heterocyclic N-halamines. In other embodiments, the device achieves a concentration of not more than about 5 ppm over a time period of about 6 hours of the one or more heterocyclic N-halamines. In other embodiments, the device achieves a concentration of not more than about 2 ppm over a time period of about 6 hours of the one or more heterocyclic N-halamines. In other embodiments, the device achieves a concentration of not more than about 1 ppm over a time period of about 6 hours of the one or more heterocyclic N-halamines. In other embodiments, the device achieves a concentration of not more than about 0.5 ppm over a time period of about 6 hours of the one or more heterocyclic N-halamines.

The porous or permeable membrane or material allows the slow release of low concentrations of water-solubilized heterocyclic N-halamines into the aquatic habitat in a time dependent manner that is believed to acclimate the aquatic species to the heterocyclic N-halamines, such that by the time that the concentration of the heterocyclic N-halamines is effective to treat a disease, the aquatic species has acclimated to such effective level and will not die. Accordingly, one embodiment of the invention is a method for the therapeutic and prophylactic in-situ treatment of aquatic diseases using one or more heterocyclic N-halamines.

The disease or condition that can be treated by the compositions and methods described herein can be any water-borne or aquatic disease or condition that is treatable with one or more heterocyclic N-halamines. The disease can be any fungus infection or bacteria infection. The disease or condition can include ich (*Ichthyophthirius multifilis*), red streaks, milky or shedding slime, flukes, bacterial gill diseases, mouth and fin rot, clamped or torn fins, and ulcers.

The aquatic species can be a fish, a marine mammal, a shellfish, or any other aquatic species. Preferably, the compositions are suited for use in aquariums, such as for the home. However, much larger environments can also be treated. Accordingly, many of the aquatic species that can be treated with the compositions include ornamental freshwater and saltwater aquarium fishes.

Using solid forms of heterocyclic N-halamines that slowly dissolve in water over time overcomes the toxic effects of introducing ethanol-solubilized MC or broadcasting MC on the surface of the water. The controlled exposure of aquatic species to slowly increasing concentrations of heterocyclic N-halamines is believed to condition the aquatic species to the toxic effects of heterocyclic N-halamines and allows the disease causing organisms to be effectively eliminated resulting in healthy fish.

Compositions and devices described herein slowly release one or more heterocyclic N-halamines into the aquatic habitat. In contrast, and as the comparative examples below show, direct addition of MC at the levels taught in the literature into a body of water containing healthy fish results in an increased mortality rate relative to a control set of fish. To solve MC's toxic effects when broadcast or introduced all at once, MC must be gradually added to the body of water. In so doing, levels exceeding 1 ppm can be achieved without causing fish mortality. As used herein, the concentration of MC and of other heterocyclic N-halamines is reported and measured as total available chlorine (TAC). MC is considered to stably bind chlorine, nevertheless, small or negligible amounts of "free" or "residual" chlorine are still present, and the TAC can be assumed to be equivalent to the "bound" or "combined" chlorine, though it is an approximation. TAC that is measured is the sum of "free" and "bound" chlorine.

Figures 3, 4:
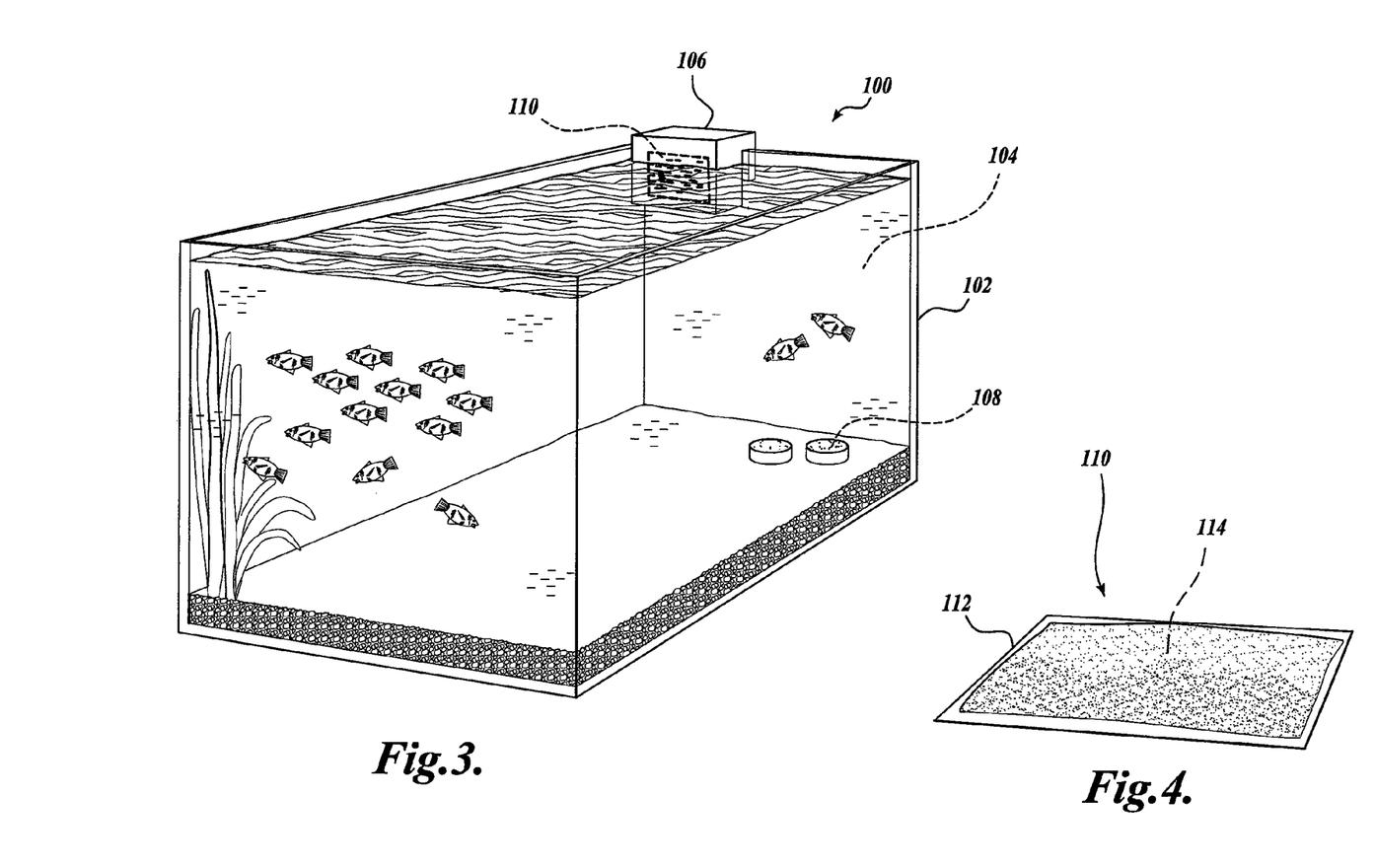
FIG. 3 is a schematic illustration of an aquatic habitat illustrating various embodiments for dosing heterocyclic N-halamines in a slow-release fashion.
FIG. 4 is a schematic illustration of a device with particulate heterocyclic N-halamines in accordance with one embodiment of the present invention.

FIG. 3 is an illustration of an aquatic habitat for a fish species. The habitat 100 can be a freshwater or saltwater aquarium tank 102, for example. Other habitats for a fish species may include natural bodies of water, such as lakes, rivers, streams, ponds, and the like. Aquatic habitats may also include a sectioned-off area of a body of saltwater.

A means for slowly raising the concentration of MC, or other heterocyclic N-halamine, in an aquatic habitat 104 for a fish species is via a solid form of MC, such as tablets 108. Tablets 108 are compacted with one or more tableting aids or carriers, such as, but not limited to magnesium sulfate, to cause the slow release of MC in the aquatic habitat. The slow release of MC is believed to sensitize or acclimate the fish to gradually increasing amounts of MC. The concentration of MC eventually rises to a level effective to treat or kill undesired organisms, but is believed to prevent killing the fish because of the acclimation of the fish to the MC.

Another means for slowly raising the level of MC, or other heterocyclic N-halamine, in an aquatic habitat for a fish species is via a device 106 within which the MC can be placed. A holder device 106 can be positioned over the top edge of the aquarium 102. The holder 106 includes a hook at the top of the holder 106 to retain the holder 106 at the edge of the aquarium 102. The holder 106 includes a bottom portion that includes a compartment for holding either a tablet form of MC, or alternatively, a packet 110 containing powder or granular MC. In the tablet form, the MC is compacted, and alternatively, can be combined with tableting aids or carriers that achieve a slow release of the MC into the aquatic habitat. In a powder or granular form, the MC can be provided within a packet device 110 that is made from a material that is either porous or permeable to water, MC, or both. Water passing through the material dissolves the powdered or granular MC which is carried through the material and into the aquatic habitat. The bottom portion of the holder 106 may have apertures, or a "grill" structure that allows the passage of water, but holds the packets 110 or tablets 108 of MC within the holder 106. The dosage of MC in the holder 106 can be controlled by closing or opening an adjustable "window" in the holder 106, which covers the area over the apertures, thus allowing more surface area of the packet 110 or tablet 108 to be exposed to water 104, or can allow greater amounts of water to circulate into the holder 106 through the apertures. Alternatively, either tablets 108 or packets 110 of MC can be placed in compartments already existing in the aquarium 102, such as the mechanical filter or the biofilter compartments.

FIG. 4 is an illustration of one embodiment of a device 110 of the present invention. The device 110 is a packet containing a heterocyclic N-halamine 114, such as MC, within the packet 110. The packet 110 is made from a porous, permeable, or semi-permeable material 112 that is capable of allowing the passage of water, and dissolved MC through the material. One embodiment of the packet 110 may be formed from two flat pieces of material 112. One or both sides of the packet 108 may be constructed from the porous or permeable material 112. Alternatively, to reduce or control the dosage of MC from the packet 110, portions of the material 112 can be covered or replaced with a nonpermeable material, so that less of the MC is exposed to the water, which allows controlling the dosage of MC.

While MC is mentioned in the above description as a representative heterocyclic N-halamine, it is to be appreciated that one or more of the heterocyclic N-halamines described herein can be used instead of or in addition to MC in the compositions and devices.

In another aspect, a method is provided for treating an aquatic habitat, comprising dosing one or more heterocyclic N-halamines into the aquatic habitat to achieve a concentration of the one or more heterocyclic N-halamines of less than about 20 ppm over a time period of about 6 hours to treat an aquatic disease. Other embodiments may have any one of the solubility profiles mentioned above.

In one embodiment, dosing may include more than one introduction of the one or more heterocyclic N-halamines. The one or more heterocyclic N-halamines can be introduced into an aquatic habitat repeatedly, either to reach an effective concentration slowly or to maintain an effective concentration in the aquatic habitat until the disease is treated or eliminated.

In another embodiment, a method is provided for treating an aquatic habitat, comprising dosing one or more heterocyclic N-halamines into the aquatic habitat to achieve a concentration of the one or more heterocyclic N-halamines of less than about 20 ppm over a time period of 6 hours to prevent an aquatic disease. For example, an aquatic species can be treated in an aquatic habitat dosed with a halogenated imidazolidinone before being introduced into another aquatic habitat. Other embodiments may have any one of the solubility profiles mentioned above.

In another embodiment, a method is provided for treating a water-borne disease by dosing one or more heterocyclic N-halamines into the aquatic habitat to produce a concentration of less than about 20 ppm of heterocyclic N-halamines over a time period of about 6 hours. Other embodiments may have any one of the solubility profiles mentioned above.

In another embodiment, a method is provided for treating a disease in an aquatic habitat that includes introducing a solid form of one or more heterocyclic N-halamines into the aquatic habitat to produce a gradual rise in the concentration of the one or more heterocyclic N-halamines in the aquatic habitat to acclimate an aquatic species. By the time the concentration of the heterocyclic N-halamines rises to a level effective to treat a pathogen, the aquatic species can be acclimated and will survive the concentration.

In other alternative embodiments, heterocyclic N-halamines may not be the only toxic materials used. Any material that is generally recognized as being toxic to both an aquatic species and an aquatic disease common to the species can be utilized in the present invention. In accordance with one embodiment of the invention, an otherwise toxic material can be used to treat a disease, provided that the toxic material is introduced in a manner that allows for the aquatic species to acclimate to the material, such that by the time that the effective level of the material is reached that treats the disease, the aquatic species will have acclimated to such level and will survive.

EXAMPLES

Example 1

Tablets containing MC were manufactured using a commercial tableting press with a composition of 7.33% wt/wt MC and 92.67% wt/wt magnesium sulfate (Mallinckrodt AR 99-100%). Magnesium sulfate was selected since it is compatible with a fish system. Finished tablets weighed between 1.44 and 1.55 grams, had a nominal diameter of ⅝-inch, and a thickness ranging from 0.238 to 0.245 inches.

Figure 1:
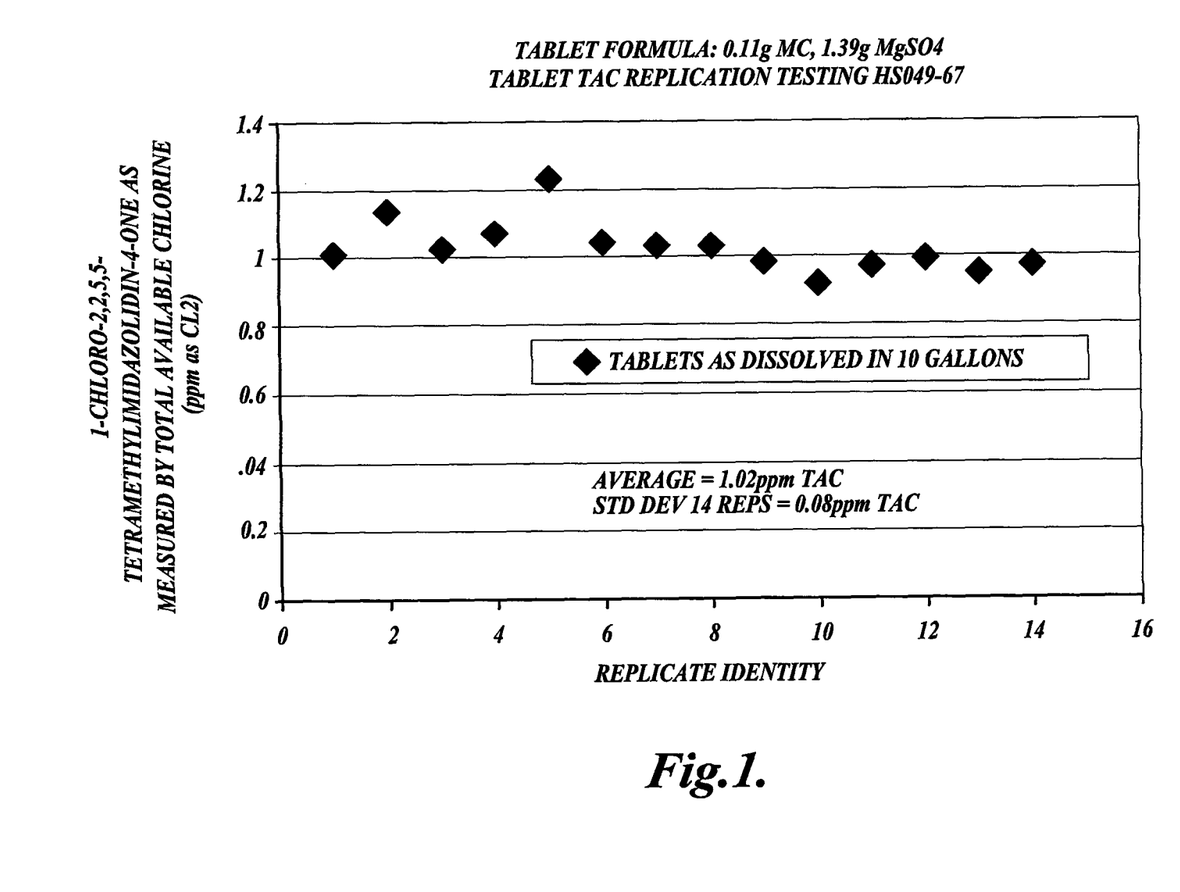
FIG. 1 is a graphical depiction of the concentration of 1-chloro-2,2,5,5-tetramethylimidazolidin-4-one as measured by total available chlorine produced by compositions made in accordance with one embodiment of the present invention.

A representative sample of 14 tablets was taken and each tablet dissolved in 10 gallons of deionized (DI) water and the total available chlorine (TAC) measured after 24 hours. FIG. 1 presents the results of the replications in which the average TAC was measured at 1.02 ppm TAC when measured using a HACH Spectrophotometer 4000U (HACH Method 8167, using HACH program 1450.) with a standard deviation of 0.08 ppm.

Figure 2:
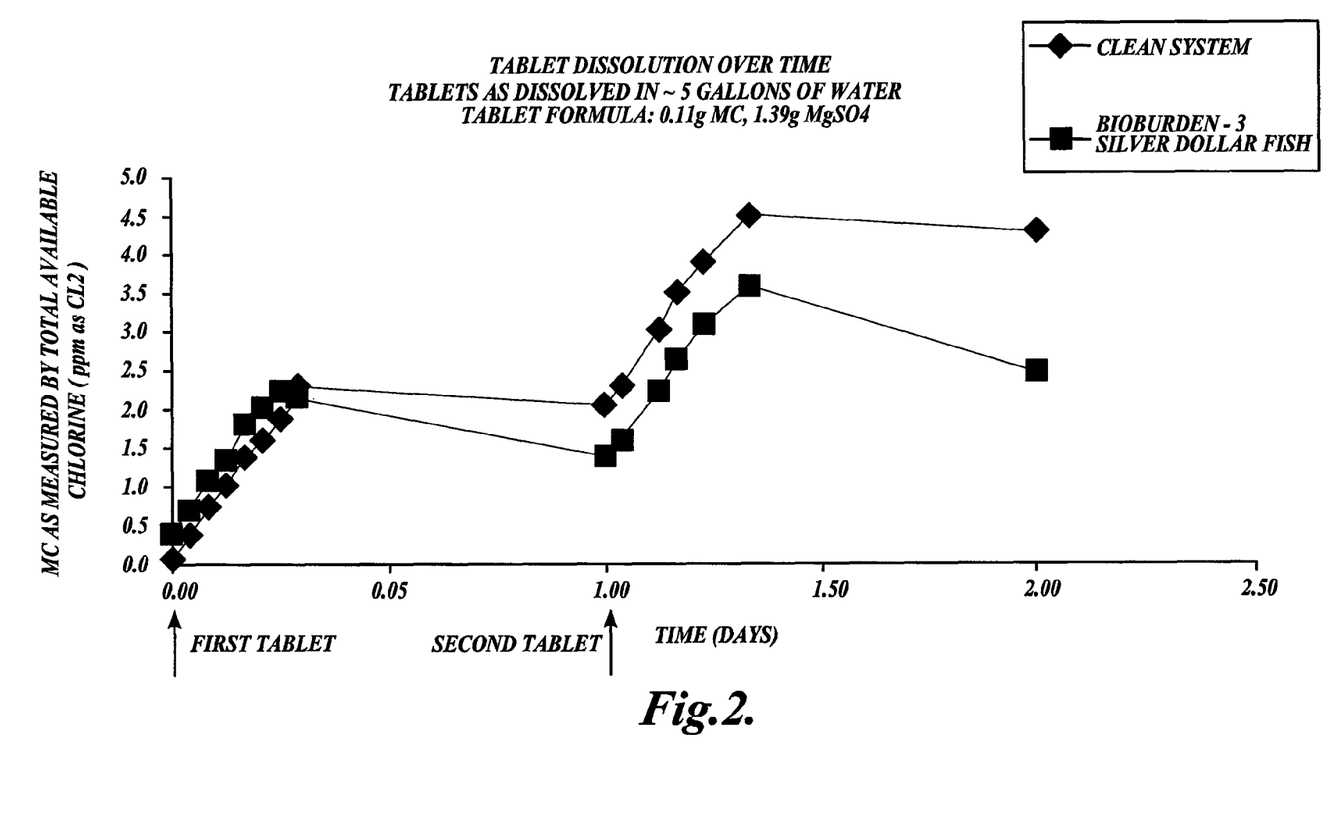
FIG. 2 is a graphical depiction of the concentration of 1-chloro-2,2,5,5-tetramethylimidazolidin-4-one as measured by the total available chlorine produced by compositions made in accordance with one embodiment of the present invention under various conditions over time.

FIG. 2 shows the elution profile of TAC when one tablet per day was added to a 5-gallon hexagonal recirculating fish tank (Marineland Eclipse Hex 5) filled with chlorine-free water with and without a bioburden (simulated by adding three silver dollar fish to the tank). The activated carbon and biofiltration devices were removed from the fish tank prior to testing. As shown in FIG. 2, the TAC levels reached their peak within 12 hours of the tablet being added to the fish tank. When another tablet was added, the levels of TAC predictably went up by the same amount as the previous day.

Comparative Example 2

A study was performed in which GlowLite (*Hemigrammus erthrozonus*) and Black Skirt Tetras (*Gymnocorymbus ternetzi*) were subjected to treatment with MC dissolved in 95% Ethanol (then diluted with water) and another set of the same fish subjected to MC tablets as described in EXAMPLE 1 dosed to equal levels of MC.

Part 1: Four 5-gallon hexagonal fish tanks were set up as follows:
  (a) Hex-1: 5 Black Skirt Tetras (Control Tank—0 ppm TAC)
  (b) Hex-2: 5 Black Skirt Tetras (Experimental Tank)
  (c) Hex-3: 11 Glow Lite Tetras (Control Tank—0 ppm TAC)
  (d) Hex-4: 11 Glow Lite Tetras (Experimental Tank)

The fish were allowed to acclimate with their surroundings for a period of three days. For the experimental tanks, 300 mg of MC dissolved in 30 g 95% EtOH followed by dilution to 100 mLs total volume with DI water was added. For the control tanks 30 g 95% EtOH diluted to 100 mLs total volume with DI water was added. TAC was measured in the experimental tanks 10 minutes after the addition of the MC solution: HEX-2=7.1 ppm TAC; HEX-4=6.0 ppm TAC. Within three hours, all 11 of the Glow Lite Tetras were dead and 3 out of 5 Black Skirt Tetras were dead. Within 24 hours the remainder of the Black Skirt Tetras were dead.

Part 2: Three 5-gallon hexagonal fish tanks were set up as follows:
  (a) Hex-1: 5 Black Skirt Tetras
  (b) Hex-3: 5 Glow Lite Tetras
  (c) Hex-4: 5 Glow Lite Tetras The fish were allowed to acclimate with their surroundings for a period of 4 hours. All tanks began with 0 ppm TAC. Tablets of MC made from 0.11 g MC pressed with 0.89 g MgSO4, with a ⅝"-diameter tablet as described in EXAMPLE 1 were added to each tank as follows:
  (a) Hex-1: 5 Black Skirt Tetras—3 tablets on day 1, 4 tablets on day 2
  (b) Hex-3: 5 Glow Lite Tetras—3 tablets on day 1, 3 tablets on day 2
  (c) Hex-4: 5 Glow Lite Tetras—2 tablets on day 1, 2 tablets on day 2

Tanks Hex-1 and 2 measured above 6 ppm TAC each day, but took approximately three hours to reach a TAC above 6 ppm. HEX 4 rose to a TAC level of 4.1 ppm TAC within the first day. No fish died throughout the 48-hour experiment.

Example 3

Five red platys (*Xiphosphorus maculatus*) were placed into an established 5-gallon hexagonal tank. The fish were observed to have whitish buildup (presumed to be fungus) on their fins. MC tablets of those described in EXAMPLE 1 were added once a day to the filter area such that the total available chlorine was maintained at 1 ppm. After 15 days, the fish appeared healthy and were observed not to have the white residue on their fins.

Example 4

Six black widow tetras (*Gymnocorymbus ternetzi*) were placed into an established 5-gallon hexagonal tank. The fish had ragged, damaged fins. MC tablets like those described in EXAMPLE 1 were added daily to the filter at such a rate as to keep the total available chlorine at 1-ppm. After six days, the fish appeared healthy and their fins appeared normal. None of the fish died during the course of the experiment.

Example 5

Four tiger Oscars (*Astronotus ocellatus*) were placed into an established 6-gallon rectangular tank (Marineland Eclipse System Six). The fish were observed to have white spots on their body and fins. One tablet containing 0.05 g MC and 0.45 g MgSO4 was added to the filter each day. The total chlorine was maintained between 0-0.5 ppm (with the exception of one day, where it was 2 ppm.) After two weeks, the appearance of the fish had not changed. Two tablets containing 0.1 g MC and 0.9 g MgSO4 were added on day 15 (a total chlorine addition of 4 ppm,) and four of these tablets were added on day 16 (a total chlorine addition of 8 ppm). Because a chlorine demand existed in the tanks, the total available chlorine actually measured did not exceed 1 ppm. Three days later the fish were observed not to have any white spots on their bodies or fins.

Example 6

Three silver dollars (*Metynnis rooseveltii*) were placed into an established 5-gallon hexagonal tank. The fish were observed to have fins with a "ragged" appearance. One tablet containing 0.05 g MC and 0.45 g MgSO4 was added to the filter each day. This maintained the total chlorine between 1-3 ppm. After 10 days, the fish appeared healthy and the fins had mostly recovered.

Example 7

Three bleeding heart tetras (*Hyphessobrycon erythrostigma*) were placed into an established 5-gallon hexagonal tank. The fish were observed to have whitish residue on their fins (presumably fungus). For the first nine days, one tablet containing 0.05 g MC and 0.45 g MgSO4 was added to the filter each day. Total chlorine was measured between 2-4 ppm. The fish did not appear to be recovering, so the dose was increased. Tablets containing 0.1 g MC and 0.9 g MgSO4 were added throughout the remainder of the experiment, as needed, to maintain 3-4 ppm total available chlorine (as measured). The fish were observed to have made a full recovery at the end of 16 days.

Example 8

Two fantail goldfish (*Carassius auratus*) were placed into an established 6-gallon rectangular tank. The fish were observed to have whitish residue on their fins (presumed to be fungus.) One tablet containing 0.05 g MC and 0.45 g MgSO4 was added to the filter each day for one week. With this dose, the total available chlorine was maintained between 0-1 ppm. After one week, the appearance of the fish had not changed. Two tablets containing 0.1 g MC and 0.9 g MgSO4 were added on day 8 (a total chlorine addition of 4 ppm), and four of these tablets were added on day 9, and 12 (a total chlorine addition of 8 ppm.) Because a chlorine demand existed in the tanks, the total available chlorine actually measured did not exceed 1 ppm. The fish were treated for an additional week, adding tablets as necessary to maintain the total available chlorine at 4 ppm measured as total available chlorine. After the final treatment, the fish appeared healthy, and where the fungus had been present, the fins of the fish had turned black.

Example 9

Five yellow rainbow fish with clear signs of ich (the majority of the bodies of the fish were covered with white spots) were placed into an established 5-gallon hexagonal tank. Tablets containing 0.1 g MC and 0.9 g MgSO4 were added throughout the duration of the experiment, as needed, to maintain approximately 3-4 ppm total available chlorine as measured. The fish were observed to have made a full recovery within a week's time after the final tablet treatment.

Example 10

The fish of EXAMPLE 9 were removed from the treated tank and placed into a clean tank. A healthy goldfish (*Carassius auratus*) was then placed into the treated tank of EXAMPLE 9 and observed for signs of ich or formation of other fish diseases. No tablets were added to the tank over the course of the experiment. The goldfish was fed and maintained as the other fish in the experiments described herein for over three months. After the end of the three months, the goldfish did not show any signs of ich.

While the preferred embodiment of the invention has been illustrated and described, it will be appreciated that various changes can be made therein without departing from the spirit and scope of the invention.

The invention claimed is:

1. A composition for treating an aquatic habitat, comprising 100% by weight, in combination, of an effective amount of 1-chloro-2,2,5,5-tetramethyl-4-imidazolidinone and magnesium sulfate, wherein the composition is bound by compression and dissolves to produce a slow rise of the imidazolidinone concentration to achieve a concentration of not more than about 20 ppm over a time period of about 6 hours in the aquatic habitat to treat a disease of an aquatic species.

2. The composition of claim 1, wherein the concentration achieved is not greater than about 1.0 ppm.

3. The composition of claim 1, wherein the concentration achieved is not greater than about 2 ppm.

4. The composition of claim 1, wherein the composition is formed into a tablet, pellet, or block.

5. The composition of claim 1, wherein the disease is *Ichthyophthirius multifilis*, fin rot, a fungus infection, or a bacteria infection.

6. The composition of claim 1, comprising 10% or less by weight of 1-chloro-2,2,5,5-tetramethyl-4-imidazolidinone and 90% or more by weight of magnesium sulfate.

7. A tablet, comprising the composition of claim 1.

8. A method for treating a disease in an aquatic habitat, comprising dosing a composition comprising 100% by weight, in combination, of an effective amount of 1-chloro-2,2,5,5-tetramethyl-4-imidazolidinone and magnesium sulfate into the aquatic habitat, wherein the composition is bound by compression and dissolves to achieve a concentration of the imidazolidinone of not more than about 20 ppm over a time period of about 6 hours in the aquatic habitat to treat a disease of an aquatic species.

9. The method of claim 8, wherein the disease is *Ichthyophthirius multifilis*, fin rot, a fungus infection, or a bacteria infection.

10. A method for treating an aquatic species suffering from a water-borne disease, comprising dosing a composition comprising 100% by weight, in combination, of an effective amount of 1-chloro-2,2,5,5-tetramethyl-4-imidazolidinone and magnesium sulfate into an aquatic habitat of the aquatic species, wherein composition is bound by compression and dissolves to achieve a concentration of less than about 20 ppm of the imidazolidinone over a time period of about 6 hours.

11. A device to treat an aquatic habitat, comprising:
a receptacle to hold a composition comprising 100% by weight, in combination of an effective amount of 1-chloro-2,2,5,5-tetramethyl-4-imidazolidinone and magnesium sulfate;
the imidazolidinone is within said receptacle; and
means for controlling the release of said imidazolidinone from said device to achieve a concentration of not more than about 20 ppm of the imidazolidinone over a time period of about 6 hours.

12. The device of claim 11, wherein the device comprises a porous or permeable material and the imidazolidine is contained within the material to allow said imidazolidinone to flow out from said device into the aquatic habitat.

13. The device of claim 11, comprising a membrane or material separating the imidazolidinone from the aquatic habitat that controls the release of the imidazolidinone.

14. The device of claim 11, wherein the means comprises a semi-permeable membrane designed to selectively allow the passage of dissolved compounds and prevent the passage of nonsolubilized compounds.

* * * * *

UNITED STATES PATENT AND TRADEMARK OFFICE
CERTIFICATE OF CORRECTION

PATENT NO. : 8,563,587 B2  
APPLICATION NO. : 12/280786  
DATED : October 22, 2013  
INVENTOR(S) : M. A. Bridges et al.

It is certified that error appears in the above-identified patent and that said Letters Patent is hereby corrected as shown below:

In the Claims

| COLUMN | LINE | ERROR |
|---|---|---|
| 14 (Claim 2, | 63 line 2) | "1.0 ppm" should read --10 ppm-- |

Signed and Sealed this
Twenty-ninth Day of April, 2014

Michelle K. Lee
*Deputy Director of the United States Patent and Trademark Office*